US010624867B2

(12) United States Patent
Varadi et al.

(10) Patent No.: US 10,624,867 B2
(45) Date of Patent: Apr. 21, 2020

(54) TRANSDERMALLY-DELIVERED COMBINATION DRUG THERAPY FOR PAIN

(71) Applicant: BioChemics, Inc., Danvers, MA (US)

(72) Inventors: Gyula Varadi, Watertown, MA (US); Zhen Zhu, Andover, MA (US); John J. Masiz, Topsfield, MA (US); Stephen G. Carter, Andover, MA (US)

(73) Assignee: Biochemics, Inc., Danvers, MA (US)

( * ) Notice: Subject to any disclaimer, the term of this patent is extended or adjusted under 35 U.S.C. 154(b) by 0 days.

(21) Appl. No.: 15/974,796

(22) Filed: May 9, 2018

(65) Prior Publication Data
US 2018/0325851 A1 Nov. 15, 2018

Related U.S. Application Data

(60) Provisional application No. 62/506,224, filed on May 15, 2017.

(51) Int. Cl.
*A61K 31/192* (2006.01)
*A61K 31/197* (2006.01)
*A61P 29/00* (2006.01)
*A61P 23/02* (2006.01)
*A61K 9/00* (2006.01)
*A61K 45/06* (2006.01)
*A61K 31/195* (2006.01)
*A61P 25/02* (2006.01)

(52) U.S. Cl.
CPC .......... *A61K 31/192* (2013.01); *A61K 9/0014* (2013.01); *A61K 31/195* (2013.01); *A61K 45/06* (2013.01); *A61P 25/02* (2018.01); *A61K 2300/00* (2013.01)

(58) Field of Classification Search
CPC .. A61K 9/0014; A61K 31/197; A61K 31/167; A61K 31/196; A61K 31/192; A61K 2300/00; A61P 23/02; A61P 29/00
See application file for complete search history.

(56) References Cited

U.S. PATENT DOCUMENTS

| 2010/0226972 | A1 | 9/2010 | Lutz |
| 2013/0123320 | A1 | 5/2013 | Chervinsky |
| 2015/0359740 | A1 | 12/2015 | Ray, II |
| 2016/0058725 | A1 * | 3/2016 | Carter .................. A61K 31/192 514/86 |

FOREIGN PATENT DOCUMENTS

| WO | WO 2011/075688 | 6/2011 |
| WO | WO 2013/048453 | 4/2013 |
| WO | WO 2014/144712 | 9/2014 |

OTHER PUBLICATIONS

Somberg et al., "Retrospective Evaluation on the Analgesic Activities of 2 Compounded Topical Creams and Voltaren Gel in Chronic Noncancer Pain," Am. J. Ther. Sep.-Oct. 2015; 22(5): 342-9. PMID: 26352120. (Year: 2015).*
Cline et al., "Compounded Topical Analgesics for Chronic Pain," Dermatitis Sep.-Oct. 2016; 27(5): 263-71. PMID: 27649348. (Year: 2016).*
Dahl et al., "'Protective premedication': an option with gabapentin and related drugs? A review of gabapentin and pregabalin in in the treatment of post-operative pain," Acta Anaesthesiol. Scand. Oct. 2004;48(9):1130-36. PMID: 15352959. (Year: 2004).*
Alexander, et al., "Transdermal gel in the treatment of postoperative pain," International Journal of Pharmaceutical Compounding, vol. 11, No. 3, pp. 181-184, May 2007.
International Searching Authority, International Search Report—International Application No. PCT/US2018/031729, dated Jul. 27, 2018 together with the Written Opinion of the International Searching Authority, 16 pages.
Plaza-Villegas, et al., "Topical pregabalin and diclofenac for the treatment of neuropathic orofacial pain in rats," Oral Surgery, Oral Medicine, Oral Pathology and Oral Radiology, vol. 114, No. 4, pp. 449-456, Oct. 2012.

* cited by examiner

*Primary Examiner* — Theodore R. West
(74) *Attorney, Agent, or Firm* — Sunstein LLP

(57) ABSTRACT

The invention provides a topical formulation for treating pain comprising a nonsteroidal anti-inflammatory agent or a Cox-2 inhibitor and a gabapentin family member.

12 Claims, 5 Drawing Sheets
(5 of 5 Drawing Sheet(s) Filed in Color)

Figs 1A-1C: Thermal (Radiant Heat) CFA Set A
1A: Day 3
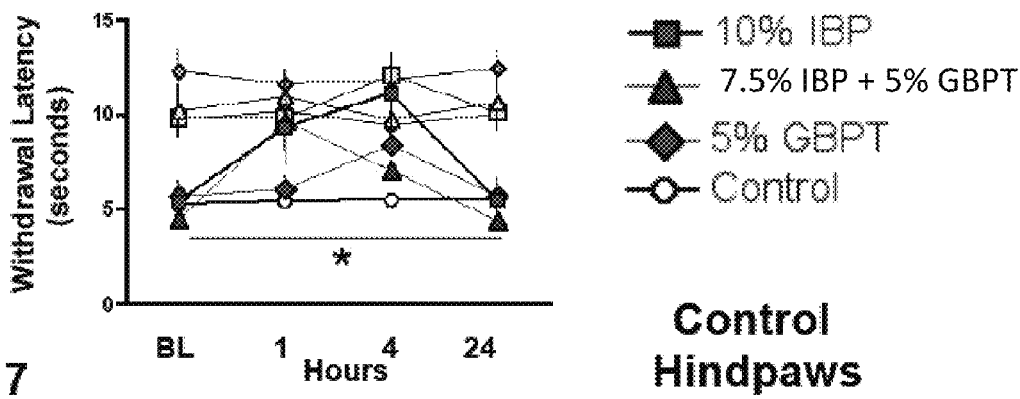
Inflamed Hindpaws
- 10% IBP
- 7.5% IBP + 5% GBPT
- 5% GBPT
- Control
1B: Day 7
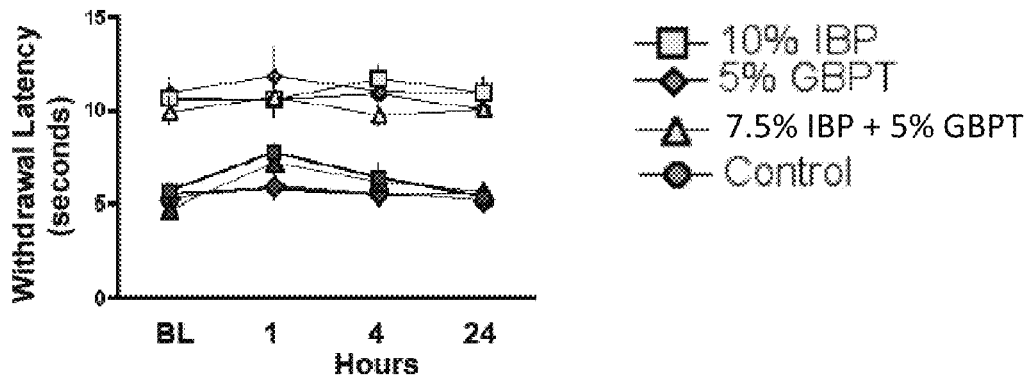
Control Hindpaws
- 10% IBP
- 5% GBPT
- 7.5% IBP + 5% GBPT
- Control
1C: Day 12
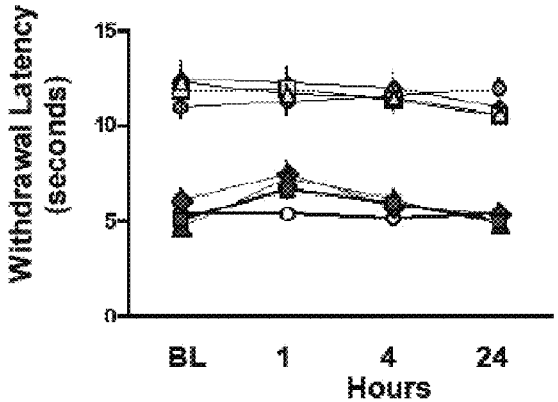

Figs 2A-2C: Mechanical (von Frey simulation) CFA Set A
2A: Day 3
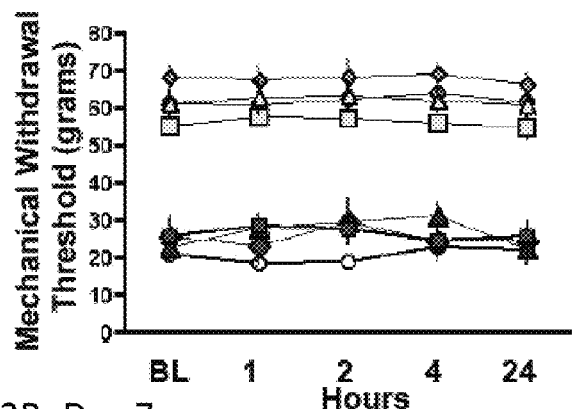
2B: Day 7
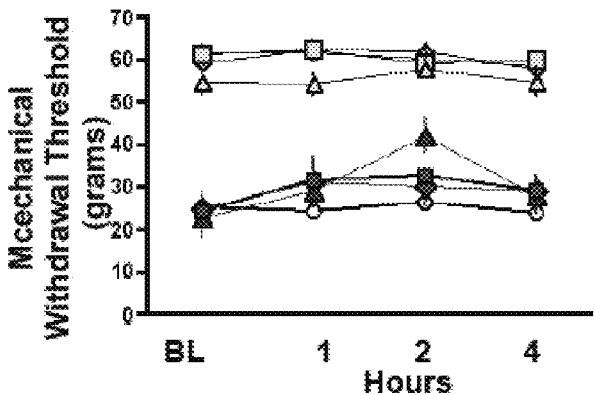
2C: Day 12
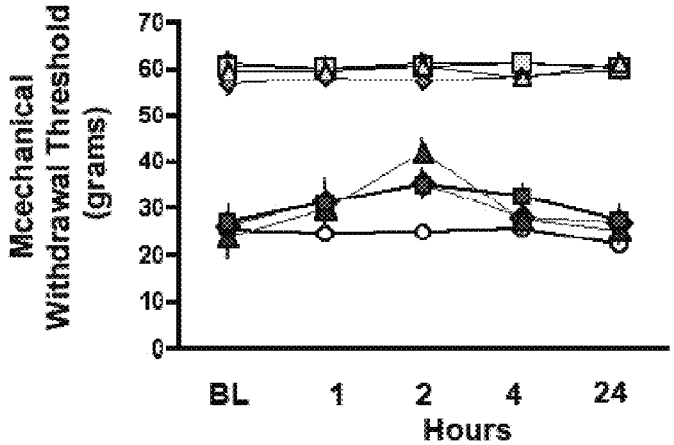

Figs 3A-3C: Thermal (radiant heat) SNI set A
3A: Day 6
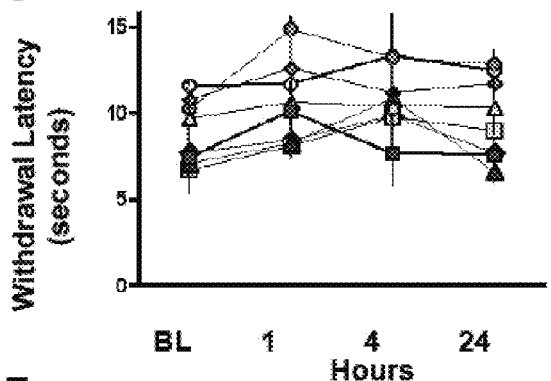
3B: Day 7
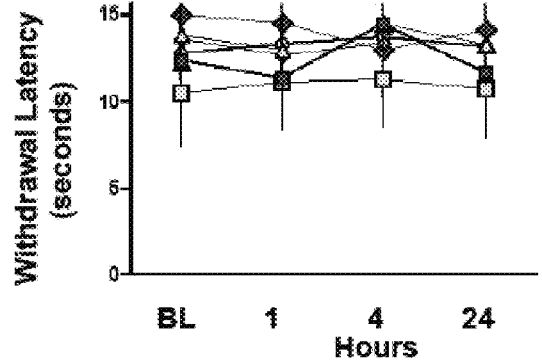
3C: Day 21
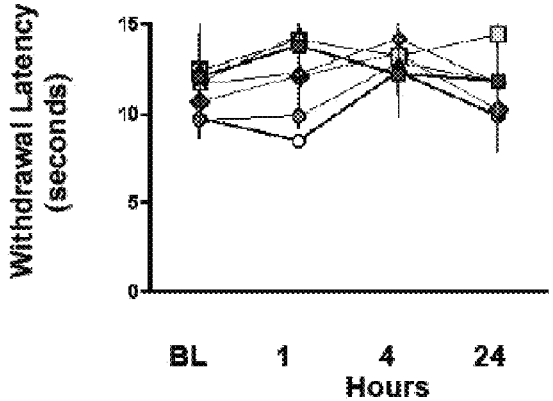

Figs 4A-4C: Mechanical (von Frey simulation) SNI set A
4A: Day 6
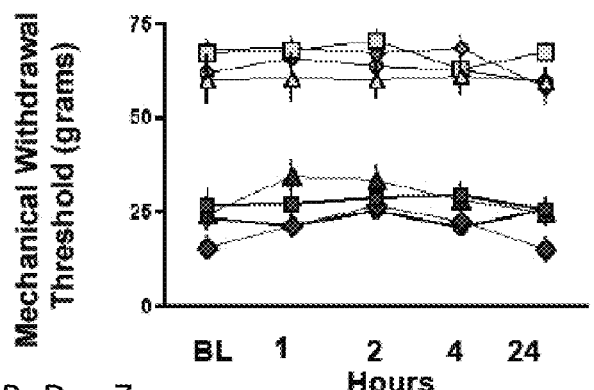
4B: Day 7
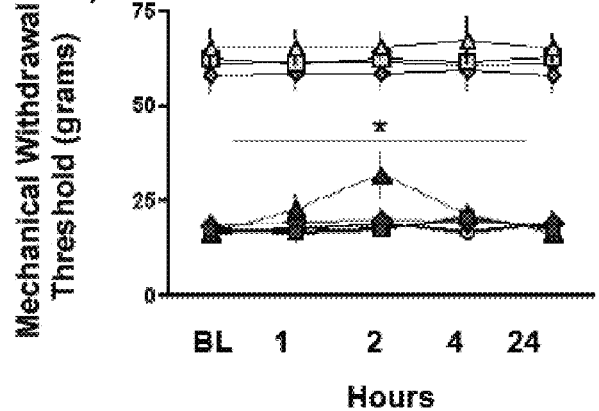
4C: Day 21
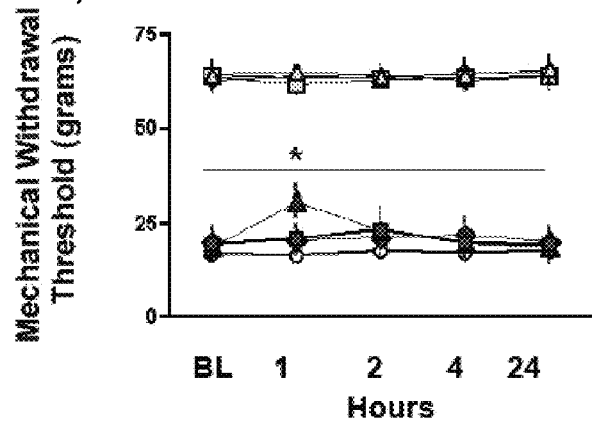

Figs 5A-5C: Mechanical (von Frey simulation) SNI set B
5A: Day 7
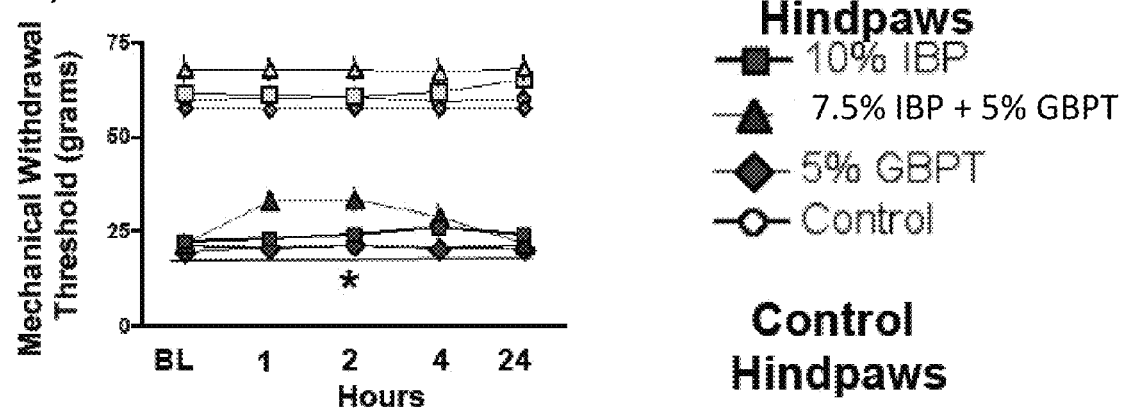
5B: Day 14
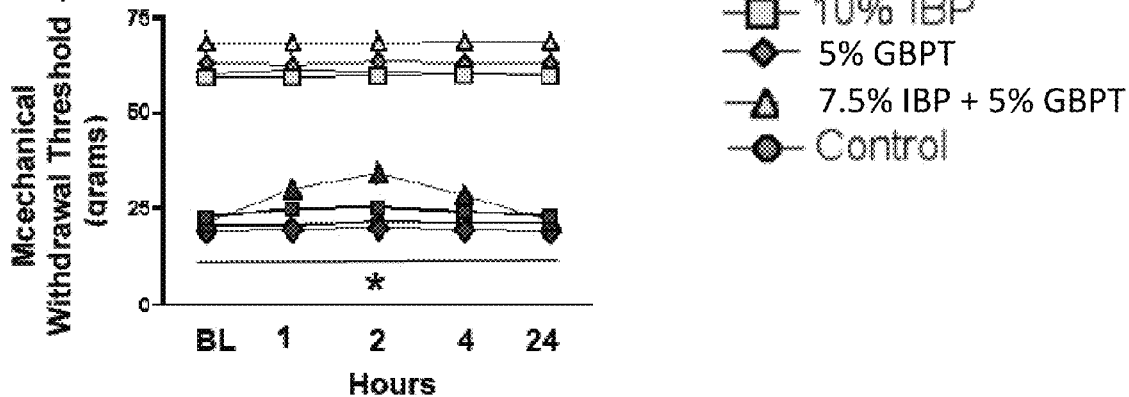
5C: Day 21
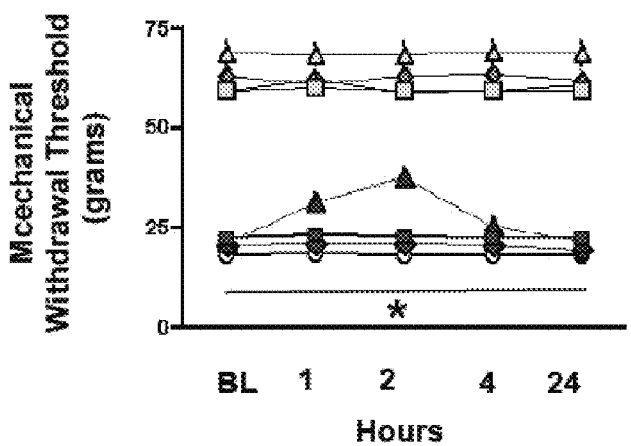

TRANSDERMALLY-DELIVERED COMBINATION DRUG THERAPY FOR PAIN

CROSS-REFERENCE TO RELATED APPLICATION

This application for United States patent claims priority to U.S. Provisional Patent Application Ser. No. 62/506,224, filed on May 15, 2017, which is incorporated herein by reference in its entirety.

TECHNICAL FIELD

The present invention relates to a combination of 2 classes of drugs that when transdermally delivered for the treatment of severe chronic or acute peripheral pain have an augmented effect on reducing pain in a non-addictive manner.

BACKGROUND

More than 100 million Americans experience a pain episode that lasts for weeks to years. Annual expenditures related to pain are higher than those for cancer, heart disease, and diabetes combined. One of the most significant indicators of the need for new pain medicines is the opioid epidemic in the US and globally. Essentially, opioids have been overprescribed to treat severe chronic and acute pain and the results have been devastating. Opioid addiction has become an epidemic effecting people from all walks of life. Recently, the CDC estimated that opioid addiction, results in over 70 deaths per day in the United States.

Pain management of severe acute or chronic peripheral pain is a complex issue that impacts the entire nervous system. Basically, an intact central nervous system (CNS) is required for the conscious perception of pain; however, blocking this perception with centrally acting drugs presents a higher risk of adverse effects. The blockade of nociceptive input into the CNS can effectively relieve or markedly attenuate discomfort and pain, revealing the importance of ongoing peripheral input to the maintenance of chronic pain. Thus, as used herein, to "treat pain" is simply meant to relieve or markedly attenuate or alleviate discomfort and pain. Thus, the development of peripherally acting pain management schemes and formulations is highly desired. Szallasi, A., et al., The Vanilloid Receptor TRPV1: 10 Years from Channel Cloning to Antagonist Proof-of-Concept, *Nature Revs. Drug Disc.*, 6: 357-372, 2007; Moran, M. M., et al., Transient Receptor Potential Channels as Therapeutic Agents. *Nature Revs. Drug Disc.*, 10: 601-620, 2011; Woolf, C. J., Overcoming Obstacles to Developing New Analgesics, *Nature Medicine*, 16: 1241-1247, 2010. Accordingly, there is a current focus on nociceptors: their role in initiating and maintaining pain might present a new very effective target for development of novel pain therapeutic approaches. Szallasi, A., et al., The Vanilloid Receptor TRPV1: 10 Years from Channel Cloning to Antagonist Proof-of-Concept, *Nature Revs. Drug Disc.*, 6: 357-372, 2007; Patapoutina, A., et al., Transient Receptor Potential Channels, *Nature Revs. Drug Disc.*, 8: 55-68, 2009; Vriens, J., et al., Pharmacology of Vanilloid Transient Receptor Potential Cation Channels, *Mol. Pharmacol.*, 75: 1262-1279, 2009; Moran, M. M., et al., Transient Receptor Potential Channels as Therapeutic Agents. *Nature Revs. Drug Disc.*, 10: 601-620, 2011; Woolf, C. J., Overcoming Obstacles to Developing New Analgesics, *Nature Medicine*, 16: 1241-1247, 2010. The central terminals of nociceptors represent important drug targets as this area contains receptors that can alter neurotransmitter release: e.g. G protein-coupled receptors, GABA receptors and voltage-gated calcium channels can effectively be modulated by existing and well-tested pharmacons The current understanding of the heterogeneity of mechanisms that contribute to the transition from acute tissue insult to chronic pain and to pain conditions with various underlying pathological status has advanced significantly in the past decade. Caterina, M. J. et al., Molecular Biology of Nociceptors, *The Neurobiology of Pain* (eds. Hunt, S. & Koltzenburg, M.) 1-33, Oxford Univ. Press, Oxford, 2005; Basbaum, A. I. et al., Molecular Mechanisms of Pain, *Cell* 139: 267-284, 2009; Kuner, R. Central Mechanisms of Pathological Pain, *Nature Medicine*, 16: 1258-1266, 2010; Costigan, M., et al., Neuropathic Pain: A Maladaptive Response of the Nervous System to Damage, *Annu. Rev. Neurosci.* 32: 1-32, 2009; Gold, M. S. and Gebhart, G. F., Nociceptor Sensitization in Pain Pathogenesis, *Nature Medicine* 16: 1248-1257, 2010.

The fundamental sensations to sense touch and pain originate in peripheral sensory neurons, which possess signaling pathways that translate environmental stimuli into neural activity. Families of ion channel proteins have been identified that serve as sensors for temperature and other noxious stimuli in primary afferent nociceptors, initiating action potentials in the peripheral terminals that ultimately release pronociceptive neurotransmitters from their central terminals to activate secondary, nociceptive spinal cord neurons. Szallasi, A., et al., The Vanilloid Receptor TRPV1: 10 Years from Channel Cloning to Antagonist Proof-of-Concept, *Nature Revs. Drug Disc.*, 6: 357-372, 2007; Patapoutina, A., et al., Transient Receptor Potential Channels, *Nature Revs. Drug Disc.*, 8: 55-68, 2009; Vriens, J., et al., Pharmacology of Vanilloid Transient Receptor Potential Cation Channels, *Mol. Pharmacol.*, 75: 1262-1279, 2009; Moran, M. M., et al., Transient Receptor Potential Channels as Therapeutic Agents. *Nature Revs. Drug Disc.*, 10: 601-620, 2011

Painful peripheral neuropathy is associated with several systemic illnesses (e.g. diabetes, cancer and HIV infection) and motivates approximately 25-50% of all pain clinic visits. Currently, LYRICA® (pregabalin, sold by Pfizer, Inc.) is approved by the FDA in the form of capsules for the management of diabetic neuropathic pain, and its congener gabapentin is similarly useful. Gabapentinoids are effective analgesic agents in neuropathic and inflammatory pain systemically and intrathecally. (Cheng, J K and Chiou, L C, *J. Pharmacol. Sci.*, 100: 471-486, 2006). Recent evidence suggests that these drugs modulate the trafficking step of $\alpha_2/\delta$ auxiliary subunit of voltage-gated calcium channels from the cell soma to the terminals (Taylor C. P., supra; Hendrich, J., et al., supra; Bauer, C. S., et al., *J. Neurosci.*, 29: 4076-4088, 2009), thereby decreasing exocytosis at the presynaptic terminal. (Christopherson, K. S., et al., *Cell*, 120: 421-433, 2005; Eroglu, C., et al., *Cell*, 139: 380-392, 2009. Neely, G. G., et al., *Cell*, 143: 628-638, 2010; Hoppa, M. B., et al., *Nature*, 486: 122-126, 2012; Marimoto, S., et al., *J. Pharmacol. Sci.*, 118: 455-466, 2012; Patel, R., et al., *J. Neurosci.* 33: 1612-1646, 2013). Thus, topical application of gabapentin at the painful area might allow access to both the peripheral and central terminals of nociceptors to produce pain relief (Boardman, L. A., et al., *Obst. Gynecol.*, 112: 579-585, 2008; Plaza-Villegas, et al., *Oral Surg, Oral Med Oral Path Oral Radiol.*, 114: 449-456, 2012; Martinez, J. A., et al., *Mol. Pain*, 8: 3-20, 2012; Zur, E., *Clin. J. Pain*, 30: 73-91, 2014).

Molecular biological studies have shown that gabapentin (GBP) binds to an exofacial epitope of the $\alpha 2/\delta$-1 and α2/δ-2 auxiliary subunits of voltage-gated calcium channels. (Field M J, et al., *Proc Nat'l Acad. Sci. USA,* 103: 17537-17542, 2006; Fuller-Bicer G A, et al., *Am J Physiol Heart Circ. Physiol.,* 297: H117-24, 2009; Gee N S, Brown J P, et al., *J. Biol. Chem,* 271:5768-5776, 1996; Luo, D. Z., et al., *J. Neurosci,* 21:1868-1875, 2001). The α2/δ-1 subunits are present mainly in presynaptic terminals, and peripheral sensory nerve injury results in the up-regulation of α2/δ-1 in dorsal root ganglion (DRG) neurons (Luo, D. Z., et al., supra; Taylor C. P., *Pain,* 142: 13-16, 2009), with consequent increase in trafficking of α2/δ-1 to their terminals (Taylor C. P., supra; Hendrich, J., et al., *Proc. Natl. Acad. Sci. USA,* 105: 3628-3633, 2008). Thus, gabapentin may function therapeutically by blocking new synapse formation, presenting a rationale for its topical application.

Current treatment strategies include use of non-steroidal anti-inflammatory drugs (NSAIDs), COX-2 inhibitors, opioids, cannabinoids, sodium channel blockers, gabapentinoids, tricyclic antidepressants, selective serotonin and norepinephrine reuptake inhibitors and anti-NGF. All of the above pharmacotherapeutic strategies carry the risk of significant side effects. While new pathways, such as the NGF/TrkA, fatty acid amide hydrolase (FAAH) and enkephalinase pathways are explored by utilizing designer inhibitor drugs, only a few to none have succeeded so far to treat severe, chronic and acute pain. However, at this time, there are limited available pharmacotherapeutics or formulations that can specifically target the conditions that are also present in chronic inflammatory, maladaptive and functional pain. There is an unmet clinical need for improved, non-addictive treatments for many painful conditions. Such opportunities include pain relief in a higher percentage of patients, greater magnitude of pain relief and greater benefits for health-related quality of life.

Transdermal delivery of pain medications is an important pharmacological approach selectively targeting the affected areas and primary afferent neurons. Since these neurons serve as the initial generator of noxious impulses, inhibiting their activation or sensitization can prevent subsequent sensitizing central events (e.g. wind-up) and plasticity. Embodiments of the invention relate to transdermal drug delivery formulations that dramatically improve the local tissue delivery of active drugs and consequently carry the potential of improving management of chronic pain with reduced side effects. The compositions and methods described herein show the efficacy of using a topical cream formulation comprising ibuprofen combined with another drug such as gabapentin as active ingredients in well-characterized animal models of chronic pain.

One important part of this invention is the need to have both drugs in the combination, amalgamate in the same tissue at the same time. This is critically important with peripheral pain, especially when targeting the peripheral nerve tissue, including the first synapse. Systemic delivery is generally ineffective in accomplishing this objective. Transdermal delivery, by contrast, can be very effective in delivering both of the combinatorial drugs through the skin and into the peripheral tissue targets at the same time and in the concentrations needed to generate an augmented pain reducing effect.

The transdermal delivery of pain medication ingredients through the skin or other body surfaces is attractive to patients for a variety of reasons. In addition to convenience, transdermal formulations eliminate the "first pass liver effect", avoid the irritation and stomach bleed of the gastrointestinal tract that often accompany pills and capsules. Furthermore, transdermal delivery can increase the efficiency of a drug by targeting more of it in the tissue where the drug was needed as opposed to general systemic delivery.

Transdermal also has another important advantage in treating peripheral pain. By applying the transdermal compound in the area where it is needed, transdermal can efficiently target the tissue needing treatment and minimize systemic exposure to the drug combination. Of course, for a transdermal drug delivery formulation to be effective, it must be capable of delivering the drug or drug combination through the skin and into the peripheral tissue targets. U.S. Pat. Nos. 9,566,256 and 9,561,174 (both herein incorporated by reference in their entireties) teach a number of technologies that are efficient in delivering drug and drug combinations through the skin and these teaching are incorporated herein.

Thus, an effective treatment system for severe acute or chronic peripheral pain, must include a combination of drugs one chosen from the NSAID class and the other chosen from the gabapentin family delivered into the peripheral target tissue via transdermal technology.

SUMMARY OF THE EMBODIMENTS

This invention, includes a combination of drugs that, when delivered together and allowed to impact peripheral nerve tissue simultaneously, provide a substantially greater level of pain relief than either drug acting alone. Further, this combination is believed to provide greater pain relief than opioids and is both non addictive and does not appear to cause tolerances to develop.

This combination of drugs includes one drug taken from the NSAID class of compounds including drugs like ibuprofen, ketoprofen, naproxen etc. The other drug in the combination is taken from the gabapentin family and includes gabapentin, atagablin and pregablin.

BRIEF DESCRIPTION OF THE DRAWINGS

The patent or application file contains at least one drawing executed in color. Copies of this patent with color drawings will be provided by the Patent and Trademark Office upon request and payment of the necessary fee.

The foregoing features of embodiments will be more readily understood by reference to the following detailed description, taken with reference to the accompanying drawings, in which:

FIGS. 1A-1C are a series of line graphs showing the sensory responses to a thermal stimulus (radiant heat) following topical administration to hindpaws of rats of a formulation containing ibuprofen (square symbols), gabapentin (diamond symbols), a combination of ibuprofen and gabapentin (triangle symbols), or no active ingredient (circle symbols) on Day 3 (FIG. 1A), Day 7 (FIG. 1B), and Day 12 (FIG. 1C) following injection of CFA to the CFA-treated foot (black filled in symbols or control injection with no CFA (white filled in symbols). Note that the each animal in this experiment had one CFA treated hindpaw and (black filled in symbol) and one control hindpaw (white filled in symbol).

FIGS. 2A-2C are a series of line graphs showing the sensory responses to a mechanical stimulus (von Frey simulation) following topical administration to hindpaws of rats of a formulation containing ibuprofen (square symbols), gabapentin (diamond symbols), a combination of ibuprofen and gabapentin (triangle symbols), or no active ingredient (circle symbols) on Day 3 (FIG. 2A), Day 7 (FIG. 2B), and Day 12 (FIG. 2C) following injection of CFA to the CFA-treated foot (black filled in symbols or control injection with no CFA (white filled in symbols). Note that the each animal in this experiment had one CFA treated hindpaw and (black filled in symbol) and one control hindpaw (white filled in symbol).

FIGS. 3A-3C are a series of line graphs showing the sensory responses to a thermal stimulus (radiant heat) following topical administration to hindpaws of rats of a formulation containing ibuprofen (square symbols), gabapentin (diamond symbols), a combination of ibuprofen and gabapentin (triangle symbols), or no active ingredient (circle symbols) on Day 6 (FIG. 3A), Day 7 (FIG. 3B), and Day 21 (FIG. 3C) following SNI surgery to the Spared Nerve Injury foot (black filled in symbols or the foot that underwent sham surgery ("Control Hindpaws"; white filled in symbols). Note that the each animal in this experiment had one SNI applied hindpaw and (black filled in symbol) and one sham surgery hindpaw (white filled in symbol).

FIGS. 4A-4C are a series of line graphs showing the sensory responses to a mechanical stimulus (von Frey simulation) following topical administration to hindpaws of rats of a formulation containing ibuprofen (square symbols), gabapentin (diamond symbols), a combination of ibuprofen and gabapentin (triangle symbols), or no active ingredient (circle symbols) on Day 6 (FIG. 4A), Day 7 (FIG. 4B), and Day 21 (FIG. 4C) following SNI surgery to the Spared Nerve Injury foot (black filled in symbols or the foot that underwent sham surgery ("Control Hindpaws"; white filled in symbols). Note that the each animal in this experiment had one SNI applied hindpaw and (black filled in symbol) and one sham surgery hindpaw (white filled in symbol).

FIGS. 5A-5C are a series of line graphs showing the sensory responses to a mechanical stimulus (von Frey simulation) following topical administration to hindpaws of rats of a formulation containing ibuprofen (square symbols), gabapentin (diamond symbols), a combination of ibuprofen and gabapentin (triangle symbols), or no active ingredient (circle symbols) on Day 6 (FIG. 5A), Day 7 (FIG. 5B), and Day 21 (FIG. 5C) following SNI surgery to the Spared Nerve Injury foot (black filled in symbols or the foot that underwent sham surgery ("Control Hindpaws"; white filled in symbols). Note that the each animal in this experiment had one SNI applied hindpaw and (black filled in symbol) and one sham surgery hindpaw (white filled in symbol).

DETAILED DESCRIPTION OF SPECIFIC EMBODIMENTS

Disclosed are topical formulations comprising a first active ingredient that is a non-steroid anti-inflammatory drug (NSAID), such as ibuprofen, and a second active ingredient that is a gabapentin family member (such as gabapentin, atagabalin, or pregabalin) which have beneficial effects in treating pain in animals and human. The formulations described herein employing an anti-inflammatory ingredient (i.e., the NSAID) plus a nerve-directed ingredient (i.e., the gabapentin family member) as active ingredients Accordingly, in a first aspect, the invention provides a topical formulation for the treatment of pain, comprising as an NSAID (such as ibuprofen) as a first active ingredient and a gabapentin family member as a second active ingredient, where the first ingredient is present in the formulation an amount equivalent to about 3% to about 10% w/w ibuprofen and the second ingredient is present in the formulation an amount equivalent to about 5% to about 15% w/w gabapentin. The inventors have found that, surprisingly, a topical formulation containing an NSAID in an amount of about 3-10% w/w ibuprofen and a gabapentin family member in an amount of about 5-15% gabapentin will transdermally deliver amounts of ibuprofen and gabapentin that act synergistically together to treat pain.

As used herein, by "NSAID" or "nonsteroidal anti-inflammatory drug" is a class of drugs that provide analgesic, antipyretic, and/or anti-inflammatory effects. In some embodiments, an NSAID inhibits the activity of enzymes cyclooxygenase-1 (COX-1) and cyclooxygenase-2 (COX-2). In some embodiments, an NSADI inhibits the synthesis of prostaglandins and thromboxanes. Non-limiting NSAIDS include ibuprofen, aspirin, salicylic acid, elecoxib, diclofenac, diflunisal, etodolac, ibuprofen, indomethacin, ketoprofen, ketorolac, nabumetone, naproxen, oxaprozin, piroxicam, salsalate, sulindac, tolmetin, meloxicam, tenoxicam, droxicam, lornoxicam, phenylbutazone, isoxicam, aceclofenac, nabumetone, loxorofen, flurbiprofen, dexketoprofen, fenoprofen, dexiburpfoen, mefenamic acid, meclofenamic acid, flufenamic acid, tolfenamic acid, celecoxib, rofecoxib, valdecoxib, parecoxib, lumiracoxib, etoricoxib, firecoxib, numesulide, clonixin, and licofelone, As used herein, by "gabapentin family member" is simply a drug in the gabapentin family. In some embodiments, a gabapentin family member binds to the α2δ subunit of voltage gated calcium ion channels (e.g., the α2δ1 subunit or the α2δ2 subunit), Non-limiting gabapentin family members include gabapentin, atagabalin, imagabalin, pregabalin, gabapentin enacarbil, 4-methylpregabalin, and PD-217,014.

The formulation comprising an NSAID and a gabapentin family member can include any excipients or carriers formulations used in topical and/or transdermal delivery of a drug. Such excipients and carriers are described elsewhere. See, for example, U.S. Pat. Nos. 9,561,174 and 9,566,256. Note that the words "excipient" and "carrier" can be used interchangeably.

In some embodiments, the present disclosure is based on the discovery that a topical formulation comprising a combination of gabapentin and ibuprofen will alleviate pain more effectively than either a formulation containing only ibuprofen or a formulation containing only gabapentin.

Embodiments described herein can be useful for treatment of all pain conditions including traumatic local pain (e.g., from a broken wrist), transient pain (e.g., fibromyalgia, muscle aches or a soft tissue injury), and/or chronic pain (e.g., peripheral neuropathy, rheumatoid arthritis). In some embodiments, the formulation can be applied to a region of the skin directly overlaying or near to the site of the pain.

The further aspects, advantages, and embodiments of the invention are described in more detail below. The definitions used in this specification and the accompanying claims shall have the meanings indicated, unless the context clearly otherwise requires. Any conflict between an art-understood definition of a word or phrase and a definition of the word or phrase as specifically taught in this specification shall be resolved in favor of the latter. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present disclosure pertains, unless otherwise defined. Reference is made herein to various methodologies and materials known to those of skill in the art. The published patents, patent applications, websites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. *Ansel's Pharmaceutical Dosage Forms and Drug Delivery Systems* (9$^{th}$ Ed.), eds. L. V. Allen, Jr., N. G. Popovich, and H. C. Ansel, Lippincott Williams & Wikins, 2011, J. P. Remington, *Remington: The Science and Practice of Pharmacy* (21*st Ed.*), ed. Randy Hendrickson, Lippincott Williams & Wilkins, 2005, *Remington: The Science and Practice of Pharmacy*, Pharmaceutical Press; 22nd Revised edition (Sep. 3, 2012), and *Transdermal and Topical Drug Delivery Systems*, eds. T. Ghosh, W. Pfister, and S. I. Yum., CRC Press, 1997.

As used herein, "pain" is meant any type of physical suffering or discomfort that may be caused, for example, by injury or illness. In some embodiments, the pain is localized to a particular part of the body. For example, a human patient who has broken her arm during a fall may have localized pain in the broken arm. In another example, a human patient who had surgery to remove a growth in his abdomen may have localized pain in his stomach. The pain may be transient or persistent, and/or may be of limited duration or chronic. Transient pain may occur, for example, when a previously broken but healed bone is occasionally painful when the person bends her arm in a certain way (e.g., while lifting a weight over her head). Persistent pain may occur when, for example, a healing process of an injury is painful, or when a patient is suffering from a disease (e.g., an autoimmune disease) that causes pain (e.g., arthritis). Chronic pain is, by definition, any pain that lasts for more than twelve weeks. Some causes of chronic pain include, for example, pain that is neuropathic, inflammatory, HIV-associated, chemotherapy-induced, or associated with cancer. The present invention is directed to all types of pain.

As used herein, by the term "treat", as in treating pain, is meant that the patient to whom the topical formulation is applied has relief of the discomfort of pain at or near the site of the application of the topical formulation.

As used herein, by the term "treated patient" is meant a patient to whom the composition described herein is administered. In some embodiments, the treated patient has localized pain or systemic pain. The pain may be transient or chronic, and may have been caused by an injury or by a disease (e.g., cancer or arthritis). Chronic can be either local or systemic. "Transient" pain is any pain that is less than twelve weeks (e.g., lasts one minute to eleven weeks, six days, twenty-three hours, and 59 minutes).

As used herein, by a "patient" is simply a multicellular organism having skin and to whom a formulation as described herein may be applied. The words "subject" and "patient" are used interchangeably. Thus, a patient includes, without limitation, both vertebrate and invertebrate animals. Non-limiting patients include humans, non-human primates (e.g., chimpanzees), laboratory animals (e.g., mice, guinea pigs, rats, rabbits), domesticated animals (e.g., cats, dogs, horses, and pigs).

In some embodiments, the formulation is topically applied to the site at or near the site of pain in the patient. For example, if the patient has elbow pain from, for example, rheumatoid arthritis, the formulation described herein can be topically applied to the skin of the elbow. By "near" is simply meant not more than 9 inches from the site of pain.

As used herein, by "topical" is meant application of a formulation to skin of a patient or to the surface of the body of the patient, or to the surface of an organ or tissue of a patient, wherein the topically applied formulation moves through the skin transdermally into the underlying tissue. The term "topical" also includes application of a formulation to a mucosal membrane of a patient (e.g., the vagina, eyes, ears, and via the alimentary canal including the mouth, throat. esophagus, stomach, intestines, and anus) so that the topically applied formulation moves through the mucosal membrane and into the tissue underlying the mucosal membrane. For purposes of applying a formulation, topical application to the skin shall include application to the stratum corneum, microinjection to the epidermis (such as can be achieved with microneedles), or use of sonophoresis, iontophoresis or other permeation-enhancing methods, without piercing the basement membrane that separates the epidermis from the dermis and without subsequent injection to the dermis or subcutaneous tissues underlying the dermis. For purposes of applying a formulation, topical application to a tissue surface of a tissue or an organ shall include application to the surface of the tissue, microinjection to the endothelial cell level at the tissue surface (such as can be achieved with microneedles), or use of sonophoresis, iontophoresis or other permeation-enhancing methods, without piercing the basement membrane that separates the endothelial cell layer from the underlying tissue and without subsequent injection to the tissues underlying the endothelial layer of the tissue or organ.

In some embodiments, the topical formulations described herein are able to facilitate delivery of an active ingredient through the epidermis (i.e., the outermost layer of skin) by carrying the component having an active ingredient past the cells of the epidermis and into the dermis. Components in the topical formulation facilitate this transdermal delivery. As described in U.S. Pat. No. 9,566,256 (the entire contents of which are hereby incorporated by reference), if a formulation contains components such that, when the formulation is applied topically, a condition of hypertonicity is created at the topical application site, the hypertonic condition may cause crenation of cells in the skin or in the surface of tissues and organs, which may widen interstitial channels in the skin or tissue surface, or open new channels. These widened and/or newly opened channels in the epidermis allow the component comprising the active ingredient activity in the formulation to be transmitted through the epidermis into the underlying dermis.

Note that by "skin" is meant any surface of the body of a patient containing epithelial tissues including, without limitation, body surfaces with hair follicles including facial skin, skin on the head, skin on the torso, skin on the extremities (e.g., arms and hands, and legs and feet), skin on the palms of the hand, skin on the soles of the feet, skin underneath fingernails and toenails, and mucous membrane-covered body surfaces including those surfaces lining the vagina, the anus, the rectum, the eyes, the ear canal, and the throat. In some embodiments, for hair follicle-containing skin, the skin is shaved or the hair is otherwise removed (e.g., with a depilatory cream) prior to application of a formulation as described herein. In some embodiments, for mucous membrane-covered skin (e.g., covering the surface of the eye), the skin is wiped or dried to reduce the amount of mucous prior to application of a formulation as described herein.

The formulations and methods described herein can be used in conjunction with other methodologies that do permanently damage skin cells or cells at the tissue surface. Cutting or ulceration of the skin can be employed together with the topical application.

As used herein, by an "active ingredient" or a "component comprising active ingredient activity" is meant any component of a formulation that provides pharmacological activity or other direct or contributory effect in the diagnosis, cure, mitigation, treatment, or prevention of disease. An active ingredient may also be referred to as a "drug". Note that when there are two or more active ingredients in the formulation, the formulation may still be referred as containing an active ingredient. In other words, the term "active ingredient" can also refer to more than a single component.

As used herein, "transdermal" means relating to or denoting the application of a medicine or drug that moves through the skin.

As used herein, "formulation" is a preparation or composition in which various components are combined with an active ingredient. As used herein, a formulation may be in the form of an ointment, cream, lotion, gel, salve or the like, for topical application or delivery of the active ingredient to a patient (e.g., a patient in need of the active ingredient). In some embodiments, as appropriate, a formulation is used in conjunction with a delivery system (such as a transdermal patch) impregnated with or containing the formulation and suitable for topical application.

One non-limiting formulation can contain a vasodilator, such as arginine or methyl nicotinate. Other excipients having the following functions can be included in the formulation comprising ibuprofen and gabapentin including, for example:

| Excipient | Function |
| --- | --- |
| Stearic Acid | Solubilizer |
| Stearyl Alcohol | Emulsifier |
| Olive Oil | Lipid |
| Urea | Penetration Enhancer |
| N,N-Dimethylacetamide | Solvent |
| Potassium Hydroxide | Solubilizer |
| Vitamin E TPGS | Penetration enhancer |
| Arginine | Vasodilator |
| Phenoxyethanol | Antimicrobial preservative |
| Carrageenan | Viscosity Increasing Agent |
| Methylparaben | Preservative |
| Purified Water | Solvent |
| Additional ingredients | Fragrance, emulsifier, vasodilator, preservative |

Note that since the formulation is to be topically applied, the carriers and excipients in the formulation are, in some embodiments, pharmaceutically-acceptable or pharmacologically-acceptable formulations. The phrases "pharmaceutically-acceptable" and "pharmacologically-acceptable" are used interchangeably and simply mean is any substance that can be included in the formulations described herein or the formulation itself that is physiologically acceptable to the patient (e.g., human) to whom the formulation is intended to be topically applied. In other words, a pharmaceutically acceptable formulation will, in most instances, not produce an allergic or similar untoward reaction when administered to a human. Note, of course, that some patients may react to a topical formulation that is pharmaceutically acceptable. In some embodiments, pharmaceutically acceptable carriers and excipients used in the formulations described herein are listed in the book *Remington: The Science and Practice of Pharmacy*, Pharmaceutical Press; 22nd Revised edition (Sep. 3, 2012). In some embodiments, the pharmaceutically acceptable carrier or excipient is one that has been approved by a state or federal regulatory agency for use in animals (including humans), or is listed in the U.S. Pharmacopia, the European Pharmacopia or another generally recognized pharmacopia for use in animals (including humans). In some embodiments, a pharmaceutically acceptable carrier or excipient is inert and/or does not cause an adverse and/or immune response in a typical patient.

Non-limiting pharmaceutically acceptable carriers include water, physiologically balanced saline solution (e.g., 0.9% w/v NaCl or Ringer's solution), artificial tears (e.g., liquid including water, salt, and substances such as carboxymethyl cellulose, polyvinyl alcohol, polyacrylic acid, hydroxypropyl methylcellulose (a.k.a. HPMC or hypromellose), hydroxypropyl cellulose and/or hyaluronic acid).

The formulation of the invention may comprise all pharmaceutical forms for administration including solutions, gels, lotions and creams—as well as ointments, foams, emulsions, micro-emulsions, milks, serums, aerosols, sprays, dispersions, micro-capsules and micro-particles thereof.

The formulations of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the formulation can include at least two, three, four, five, six, seven, eight, nine, ten, or all of these additional ingredients identified in the previous sentence. The amounts of such ingredients can range from 0.0001% to 99.9% by weight or volume of the formulation, or any integer or range in between.

Typically, such formulations are prepared either as topical formulations, liquid solutions or suspensions, solid forms suitable for solution in, or suspension in, liquid prior to use can also be prepared.

Non-limiting pharmaceutically acceptable excipients that can be included in the compositions described herein include excipients or carriers such as Polysorbate 20, Caprylic/Capric Glyceride, Petrolatum, Beeswax, Lecithin, Dimethicone, Alkylmethyl Siloxane, Palmitic Acid, Lanolin, Linoleic Acid, Isopropyl Myristate, Stearyl Octanoate and Cetyl Octanoate, and Polysorbate 80.

In some embodiments, a non-limiting pharmaceutically acceptable carrier that can be used in the compositions described herein is a polymeric, mucoadhesive vehicle. Examples of mucoadhesive vehicles suitable for use in the methods or formulations of the invention include but are not limited to aqueous polymeric suspensions comprising one or more polymeric suspending agents including without limitation dextrans, polyethylene glycol, polyvinylpyrolidone, polysaccharide gels, Gelrite® cellulosic polymers, and carboxy-containing polymer systems. In a particular embodiment, the polymeric suspending agent comprises a cross-linked carboxy-containing polymer (e.g., polycarbophil). In another particular embodiment, the polymeric suspending agent comprises polyethylene glycol (PEG).

Further examples of pharmaceutically acceptable excipients that can be included in the topical formulations described herein include, without limitation, inert proteins such as albumins; hydrophilic polymers such as polyvinylpyrrolidone; amino acids such as aspartic acid (which may alternatively be referred to as aspartate), glutamic acid (which may alternatively be referred to as glutamate), lysine, arginine, glycine, and histidine; fatty acids and phospholipids such as alkyl sulfonates and caprylate; surfactants such as sodium dodecyl sulphate and polysorbate; nonionic surfactants such as such as TWEEN®, PLURONICS®, or a polyethylene glycol (PEG) designated 200, 300, 400, or 600; a Carbowax designated 1000, 1500, 4000, 6000, and 10000; carbohydrates such as glucose, sucrose, mannose, maltose, trehalose, and dextrins, including cyclodextrins; polyols such as mannitol and sorbitol; chelating agents such as EDTA; and salt-forming counter-ions such as sodium. The concentration of the excipient is, typically, from 1 to 10,000 times the concentration of the active ingredient (e.g., ibuprofen or gabapentin, or both).

In further embodiments, the topical formulations described herein may include an NSAID, a gabapentin family member, and one of or combination of a few of, or all of the following ingredients: water; capric/caprylic triglyceride; shea butter; squalane; cetyl alcohol; ethyl alcohol; glycerin; butylene glycol; propylene glycol; pentylene glycol; capryl glycol; phenoxyethanol; EDTA, disodium EDTA, trisodium EDTA, EGTA, disodium EGTA, trisodium EGTA, citric acid, phosphoric acid, succinic acid; steareth-20; chlorhexidine diglunonate; potassium sorbate; methylparaben, propylparaben, butylparaben, ethylparaben, isobutylparaben; denatured alcohol; glyceryl stearate; dimethicone; PEG-100 stearate; triethanolamine; maltodextrin; sorbic acid; ethylene brassylate; methyl linalool; isobutyl methyl tetrahydropyranol; ethylhexylglycerin; hexylene glycol; dimethicone; ceramide II; stearic acid; glyceryl stearate; acrylamide/acryloyl dimethyl taurate copolymer; isohexadecane; polysorbate 80; alcohol; sodium cocoamphodiacetate; sodium methyl cocoyl taurate; isododecane; polyacrylamide/C13-C14 isoparaffin/laureth 7 mixture; PEG-12 dimethicone; and/or ethylhexyl palmitate; xanthan gum; acrylate C10-30 acrylate cross polymer; PVP/hexadecene copolymer; C12-15 alkyl benzoate; sorbitan isostearate; tocopheryl acetate; and/or prodew 400. The concentrations of any one of these ingredients can range from 0.00001 to 99% by weight or volume of the formulation or any integer or range derivable therein as explained in other portions of this specification which are incorporated into this paragraph by reference.

In some embodiments, the concentration of water can be about 35% to about 80% by weight of the formulation. The concentration of water can also be any range between 35% to 80% by weight of the formulation (e.g., between about 45% to about 70% or between about 50% to about 60%).

The formulations of the present invention can also take the form of topically spreadable formulations (e.g., creams) and sprayable formulations.

In some embodiments, the compositions described herein compositions described herein may include one or more excipients selected from among the following: a tonicity enhancer, a preservative, a solubilizer, a viscosity enhancing agent, a demulcent, an emulsifier, a wetting agent, a sequestering agent, and a filler. The amount and type of excipient added is in accordance with the particular requirements of the composition and is generally present in the composition at a concentration of between about 0.0001% to 99% w/v, or between about 0.01% to 95% w/v, or between about 0.1% to 90% w/v, or between about 1% to about 75% w/v.

Topical application of a formulation containing both ibuprofen (or other NSAID) and gabapentin (or other gabapentin-family member) can effectively enhance the delivery of the drug into the skin and promoted effective pain management by acting on the peripheral nervous system and by modulating the conduction of the nociceptive signal.

Thus, the results described herein identified a synergistic relationship between the drugs. This discovery will allow the formulation of combination therapies to access multiple mechanisms of action along with reducing overall doses, thereby providing major benefits for such therapy.

In some embodiments, the topical formulation described herein may include a vasoactive agent such as a vasodilator or a vasoconstrictor. By "vasoactive agent" is simply component in the formulation that can change the vasomotor tone to either increase or decrease blood pressure in the local peripheral area of a blood vessel near the application site of the patient being treated with the formulation. A "vasoconstrictor" will increase the blood pressure in the local peripheral area of a blood vessel near the application site of the patient being treated with the formulation. The words "vasoconstrictor" and "component with vasoconstrictory activity" are used interchangeably. Additionally, "vasoconstrictor" may refer to one or more different component each having vasoconstrictory activity. Commonly used vasoconstrictors include, without limitation, antihistiamines, amphetamines, cocaine, caffeine (and other stimulants), psilocybin, tetrahydrozoline HCL, phenylephrine, pseudoephedrine, lysergic acid diethylamide (LSD), ergine (LSA or d-lysergic acid amide), mephedrone, oxymetazoline, epinephrine, ephedrine, adenosine triphosphate, amphetamine, antazoline, asymmetric dimethylarginine, cocaine, dopamine, endothelia, hydroxyamphetamine, isoproterenol, levonordefrin, metaraminol, methamphetamine, methoxamine, methylphenidate, neuropeptide Y, naphazoline, norepinephrine, oxymetazoline, phenylephrine, pseudoephedrine, tetrahydozoline, thromboxane, tramazoline, tyramine, derivatives of these and combinations of the foregoing. A review of topical vasoconstrictors is available at Higgins et al., Laryngoscope 12(12): 422-432, 2011.

By "vasodilator" is simply meant a component that causes dilation (i.e., widening) of a blood vessel and thereby decreases the blood pressure in the local peripheral area of a blood vessel near the application site of the patient being treated with the formulation. The words "vasodilator" and "component with vasodilatory activity" are used interchangeably. Additionally, "vasodilator" may refer to one or more different component each having vasodilatory activity.

In the formulations described herein, upon topical application, the vasodilator in the formulation works to dilate the blood vessel in the skin (e.g., in the dermis) to facilitate uptake of the active ingredient (e.g., ibuprofen and gabapentin) into the tissue underlying the dermis. Commonly used vasodilators include, without limitation, adrenaline, histamine, prostacyclin, prostaglandin D2, prostaglandin E2, arginine (e.g., L-arginine), nicotinic acid (niacin or vitamin B3), bradykinin, adenosine, heparin, benzyl nicotinate, nitroglycerin, diltiazem, papaverine, tolazoline, and methyl nicotinate. Still additional vasodilators include, without limitation, amrinone, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, diisopropylammonium dichloroacetate, ethyl nicotinate, hepronicate, hexyl nicotinate, ifenprodil tartrate, inositol nicotinate, isoxsuprine hydrochloride, kallidinogenase, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, xanthinol nicotinate, diazoxide, hydralazine, minoxidil, and sodium nitroprusside.

Centrally acting agents that act as vasodilators include clonidine, quanaberz, and methyl dopa. Alpha adrenoceptor blocking agents that act as vasodilators include indoramin, phenoxybenzamine, phentolamine, and prazosin. Adrenergic neuron blocking agents that act as vasodilators include bedmidine, debrisoquine, and guanethidine. ACE inhibitors include benazepril, captopril, cilazapril, enalapril, fosinopril, lisinopril, perindopril, quinapril, and ramipril. Ganglion blocking agents that act as vasodilators include pentolinium and trimetaphan. Calcium channel blockers that act as vasodilators include amlodipine, diltiazem, felodipine, isradipine, nicardipine, nifedipine, nimodipine, and verapamil. Prostaglandins including: prostacyclin, thrombuxane A2, leukotrienes, PGA, PGA1, PGA2, PGE1, PGE2, PGD, PGG, and PGH, also act as vasodilators. Angiotensin II analogs including saralasin also act as vasodilators. Other suitable vasodilators include nitroglycerin, labetalol, thrazide, isosorbide dinitrate, pentaerythritol tetranitrate, digitalis, hydralazine, diazoxide, and sodium nitroprusside, derivatives of these and combinations of the foregoing.

The vasodilator (or mixture of vasodilators) in the formulation can be chosen from the classes of endothelium-dependent vasodilators, endothelium-independent vasodilators and prostaglandin-based vasodilators to elicit the production of endogenous prostaglandins. Prodrugs of any of the foregoing vasodilators can also be used. While not wishing to be bound by any particular theory, it may be that inclusion of the vasodilator in the formulation will relax or dilate the dermal arteries and arterioles and therefore increase the volume of blood flow into the capillary network. This increased volume of blood will subsequently result in an increased trans-capillary flux of water from the vessel into the surrounding tissue, including the epidermis. Other examples of vasodilators include nitroglycerine, arginine and some arginine derivatives, acetylcholine, sodium nitroprusside, methyl nicotinate, hexyl nicotinate, arachidonic acid, prostaglandin $D_2$, prostaglandin $I_2$, tolazoline, papaverine. Arginine is a known substrate for nitric oxide synthase and it is known that nitric oxide can exert a vasodilatory effect. However, arginine alone may be unable to penetrate to the dermis when applied topically.

In some embodiments, the formulation containing a vasodilator and a combination of ibuprofen (or other NSAID) and gabapentin (or other gabapentin family member) also contains either a chelator or an osmolyte, or both a chelator and an osmolyte.

As used herein, by "chelator" or "component having chelating activity" is meant component in the formulation that that, in the presence of an ion with a valency higher than monovalency (e.g., a divalent cation or a divalent metal cation), binds to that ion and sequesters it, effectively trapping that ion and making it unable to interact with other molecules. Typical ions having valency higher than monovalency that will be bound by and sequestered by a chelator include $Ca2+$ and $Mg2+$. Note that a chelator, as used herein, will not bind and sequester a monovalent cation such as $Na+$.

In some embodiments, the other components in the formulations described herein are selected so that they are not sequestered by the chelator. By "sequestered" is meant a chelator binds to and holds an ion having a valency higher than monovalency (e.g., holds a divalent cation) such that the bound ion is unable to freely move and function in the formulation.

Non-limiting examples of components comprising a chelating activity include BAPTA (1,2-bis(o-aminophenoxy)ethane-N,N,N',N'-tetraacetic acid), Fura-2 (see Grynkiewicz et al., J. Biol. Chem. 260(6) 3440-3450, 1985), DMSA (dimercaptosuccinic acid), ALA (alpha lipoic acid), DMPS (2,3-dimercapto-1-propanesulfonic acid), deferoxamine, deferasirox, dimercaprol, penicillamine, EDTA (ethylenediaminetetraacetic acid), EGTA (ethylene glycol tetraacetic acid), and ethylenediamineacetate. Additional chelating agents are described in U.S. Pat. No. 4,528,196 (incorporated by reference)

In some embodiments, the component with chelating activity is a divalent cation chelator. EGTA, EDTA and CDTA are non-limiting examples of divalent cation chelators. The divalent cation chelator in the formulation is present to physically separate the calcium, magnesium, and manganese as well as other divalent cations from the protein-protein bonds present in the interstitial spaces created by like-ectoproteins protruding from each adjacent cell. The removal of the divalent cation from these protein-protein interactions physically breaks the bonds holding the two adjacent cells together in the native position. The breaking of these protein-protein bonds then allows for the interstitial spaces to transiently expand, lowering the barriers to movement in the skin tissue (or other tissue at the surface of a tissue or organ) for the active ingredient (e.g., a therapeutic or diagnostic agent). As this separation of the protein-protein bond is transient, the skin cells or cells at the tissue surface are not permanently damaged by contact with the formulation comprising the chelator.

It shall be understood that more than one chelator may be contained within a formulation as described herein. It should also be noted that a chelator in a formulation described herein may serve exclusively as a chelating activity provider or it may also serve an addition function. For example, the chelator (e.g., a divalent cation chelator) may also have a vasoactive activity, or may act as an active ingredient. Certainly, the chelator within the formulation may contribute to the osmolarity of the formulation, along with the other components in the formulation, if the chelator is soluble in the formulation.

In some embodiments, the formulation described herein contains an osmolyte. A component whose main function in a formulation is to raise the osmolarity of the formulation may be referred to as an "osmolyte." In some embodiments, an osmolyte is a molecule having an affinity for water (i.e., hydrophilicity or hygroscopicity). When present in a formulation, an osmolyte is able to draw water from cells, vasculature, or other structures of the body (e.g., from the skin). In embodiments where a chelator is also present in the formulation and where the osmolyte is an ion, that ionic osmolyte cannot have a valency higher than a monovalency. For example, when an osmolyte is present in a formulation present in a chelator-containing formulation, the osmolyte cannot be a divalent cation (or a trivalent or quadvalent cation), because the chelator will complex with the divalent cation (or trivalent or quadvalent cation) and effectively sequester it and prevent is ability to function as an osmolyte.

Some non-limiting osmolytes that may be used in the formulations described herein include sorbitol and glucose. In addition to sorbitol and glucose, some other common physiologically acceptable osmolytes include (but are not limited to) sugar osmolytes such as monosaccharides (e.g., mannitol, galactitol, fucitol, iditol, inositol, glucose, fructose, galactose, ribose, rhamnose, and xylopyranose), disaccharides (e.g., maltitol, lactitol, isomalt, sucrose, lactose, maltose, trehalose, cellobiose, gentiobiose, isomaltose, kojibiose, laminaribiose, marmobiose, melibiose, nigerose, rutinose and xylobiose), and monovalent ion osmolytes (such as lithium, sodium, and potassium). Note that a monovalent ion osmolyte may be contributed by a salt comprising that monovalent ion (e.g., NaCl providing the Na+ monovalent ion osmolyte).

Without wanting to be bound by any particular mechanistic hypothesis, the hypertonicity of the formulation can cause crenation of cells in the skin or in the tissue surface at the site that the formulation is applied. This crenation can widen or open interstitial spaces in the skin or tissue surface. The component with vasoactive activity (e.g., a vasodilator) in the formulation can act on the microvasculature within the dermis to generate a vasodilation event that releases plasma and/or interstitial fluid into the interstitial spaces and extracellular spaces surrounding the vessel and into the dermis and epidermis. Thus, the high osmolarity of the formulation allows an increase in the intracellular osmotic pressure of the skin cells or cells at the tissue surface at the application site of the formulation. This increase in intracellular osmotic pressure will move water from inside the cell to the interstitial space. This action will in turn cause a decrease in the volume of the cell and conversely, increase the volume and size of the interstitial spaces.

There is an accepted range of osmolarity of vertebrate subjects defined as isotonic ranging from 240-340 milliOsmoles/Liter with a tighter range of 280-310 milliOsmoles/Liter. In other words, any formulation that has an osmolarity value of greater than about 345 milliOsmoles/Liter (or 345 mOsM) will be considered to be hypertonic to a vertebrate subject.

When the osmolarity of the entire formulation is considered, the osmolar value is calculated for each of the components in the formulation individually, and the total osmolarity of the formulation determined by adding the osmolarity of the individual components.

In further embodiments, the formulation described herein comprises a lipid component. The presence of a lipid component in the formulation may facilitate the movement of the other components through the layers of the stratum corneum and to the interface with the stratum corneum and the other layers of the epidermis. The lipid component may be in the form of a lipid-enriched stable pharmaceutical base of the formulation. See Alvarez and Rodriguez, "Lipids in Pharmaceutical and Cosmetic Preparations," *Grasas y Aceites* 51: 74-96, 2000. Non-limiting lipids that can be used include simple lipids such as vegetable oil lipids (e.g., soybean oil, olive oil, safflower oil), animal oils (e.g., fish oil), fats (e.g., shea butter), wax (e.g., bees wax, lanolin), and compound lipids such as phospholipids (e.g., diphosphatidyl glycerols, phosphatidyl cholines, phosphatidyl serines, phosphatidyl inosiols, phosphatidic acids, phosphatidyl glycerols, and phosphine analogs), sphingolipids (e.g., sphingophospolipids and sphingoglycolipids), glycolipids, and sulfolipids, and derived lipids such as fat-soluble vitamins (e.g., vitamin A, vitamin D, vitamin E, and vitamin K), prostaglandins (e.g., PGA2, PGB2, etc.), and steroids including sterols and sterol esters (e.g., cholesterol), sterylglycosides and acylsterylglycoside, sterol sulfates, and bile acids and their conjugates.

In further embodiment, the formulation described herein comprises a penetration enhancer. By "penetration enhancer" is meant a compound, particle, or other substance or material that when included in a formulation that is applied topically to the skin or to the tissue surface, increases the rate or amount of transport of an active ingredient in the formulation past the cells (living or dead) of the epidermis. Non-limiting examples of penetration enhancers include individual fatty acids, fatty acid esters, polyols, amides, various anionic, cationic and nonionic surfactants such as but not limited to sodium laurate and sodium lauryl sulfate, phospholipids, cholesterol and cholesterol derivatives, m-pyrrole, dimethyl acetamide, limonene, sphingolipids, ceramides, terpenes, alkanones, menthol, various organic acids, such as but not limited to salicylic acid, citric and succininc acid, prostaglandin, decyl methyl sulfoxide, urea, sulfoxide alcohols, plant extract oils. Suitable fatty acids include without limitation: linoleic acids, linolenic acids, oleic acids, stearic acids, and myristic acids. Phospholipids include without limitation: phosphatidylcholine, phosphatidylethanolamine, and phosphatidylserine. Plant extract oils include oils of peanut, hemp, borage, olive, sunflower, soybean, monoi and macadamia. The plant extract oil can be mixed with an alcohol such as ethyl alcohol, isopropyl alcohol, and methyl alcohol.

In further embodiments, the formulation is applied with a transpiration barrier. A "transpiration barrier" shall mean a component such as a solid patch, a hydrophobic chemical component, or a self-assembling chemical component (including components that form gels) that is capable of preventing water loss from skin or tissue surface due to transpiration when applied to the skin or tissue surface of a patient. On non-limiting transpiration barrier is simply a bandage. If a transpiration barrier is used, the pressure created by the released plasma can build at the impermeable transpiration barrier to create a second osmotic pressure event based on water influx from the vasculature. The first osmotic event upon application of a formulation described herein (e.g., containing ibuprofen and gabapentin, a vasoactive agent, a chelator or an osmolyte (or both)) is a subtle crenating process that can open up the epithelium (by widening the interstitial spaces between the cells in the epidermis) for better drug and particle movement. The second event is the creation of a bolus-type gradient of hydrodynamic pressure in the localized skin tissue or tissue surface tissue (e.g., the surface of the left ventricle of the heart) due to the presence of excessive amounts of interstitial fluid released from the microvasculature by the vasodilator with no place to go except to be re-directed back into the body.

In some embodiments, the formulation can also include solvents, excipients, preservatives, skin conditions, emulsifiers, carriers, polymers, thickeners, phospholipids, fatty acids, cholesterols, complex lipids, prostaglandins, vitamins and vitamin derivatives, antioxidants, humectants, surfactants. Other components may be included in the pharmaceutical preparation that promote passive dermal penetration of chemicals and pharmaceuticals, including urea, organic solvents, such as dimethyl sulfoxide (DMSO), and others. Yet additional components include excipients or carries such as, without limitation, water, Stearyl Alcohol, Polysorbate 20, Caprylic/Capric Glyceride, Petrolatum, Beeswax, Lecithin, Dimethicone, Alkylmethyl Siloxane, Stearic Acid, Palmitic Acid, Lanolin, Linoleic Acid, Isopropyl Myristate, Stearyl Octanoate and Cetyl Octanoate, and Polysorbate 80.

It should be noted that any component of a formulation that is not an active ingredient may be referred to as an excipient or carrier. Thus, osmolytes, solvents, fragrances, solubilizers, emulsifiers, penetration enhancers, vasodilators, vasoconstrictors, surfactants, lipids (which also includes fatty acids and oils), and chelators are all excipients.

Non-limiting pharmaceutically acceptable excipients that can be included in the formulations described herein include Stearyl Alcohol, Polysorbate 20, Caprylic/Capric Glyceride, Petrolatum, Beeswax, Lecithin, Dimethicone, Alkylmethyl Siloxane, Stearic Acid, Palmitic Acid, Lanolin, Linoleic Acid, Isopropyl Myristate, Stearyl Octanoate and Cetyl Octanoate, and Polysorbate 80.

The solvent may be polar, non-polar, aqueous, non-aqueous, organic or inorganic in composition. Common solvents include, without limitation, water and propylene glycol.

Of course, as the skilled practitioner understands, the addition of extra components to a formulation as described herein depends largely upon the form of the formulation. The formulation may be in the form of a lotion, cream, gel, paste, nanoparticle powder, spray, aerosol, or milk. Moreover, different components of the formulation may be encapsulated in a simple or complex lipid mixture for physical separation from the other component parts of the formulation, which may not be compatible with each other or for which there is a need to enhance the lipid-characteristics of the component to facilitate transmigration through the stratum corneum. Methods for encapsulating a component in a simple or complex lipid mixture are known (see, e.g., U.S. Pat. Nos. 7,867,981 and 6,406,713, both incorporated herein by reference).

As a result of using the formulations and/or application methods described herein, an expanded range of candidate transdermal active ingredients can be used. For example, by using such formulations, higher molecular weight and less hydrophobic active ingredients can be transdermally delivered.

Thus, in some embodiments, the formulation may include excipients, solvents, penetration enhancers, lipids, or other components. The formulation can also be a patch or a component of a patch or similar drug delivery device.

The formulation can be applied to the skin or tissue surface; i.e., topically (step 110). For example, the formulation can be a cream, lotion, ointment, gel, or other substance suitable for topical application to the skin or tissue surface. Optionally, the skin or tissue surface can be worked to enhance the penetration of the active ingredient past the epidermis (e.g., into or through the basement membrane). Various methods of working skin are known. For example, the skin or tissue surface may be mechanically worked in the form of massaging or sonophoresis (e.g., via ultrasound) which can exert mechanical work and enhance penetration. The skin or tissue surface may also be worked by electrical work such as iontophoresis.

Skin or tissue surface working processes that permanently damage cells may also be used, as long as the formulation itself does not cause the permanent damage. For example, the skin or tissue surface can be worked by cutting, ulceration, wound formation or piercing. For example, piercing the skin with microneedles (e.g., with a device having projections designed to pierce the stratum corneum without the substantial triggering of deeper pain receptors) can aid in the transdermal delivery process of the active ingredient. Microneedles are disclosed, for example, in U.S. Pat. No. 6,611,707, which is incorporated herein by reference in its entirety. Other methods of working the skin and tissue surfaces are commonly known.

In some embodiments, the formulation is delivered into the skin or into the tissue surface. For example, for delivery to the skin, the formulation can be injected into the epidermis with microneedles. For delivery to a tissue surface (e.g., the surface of a liver), the formulation can be injected into the endothelial cells covering the surface of the liver with microneedles. In some embodiments, the method for delivery of an active ingredient using the formulations and methods described herein includes optionally applying the formulation with a transpiration barrier. The transpiration barrier can be a water impermeable drug administration patch; for example, a sheet of water-resistant plastic with an adhesive layer or other attachment mechanism (e.g., a bandage). The patch can be applied atop a formulation applied to the skin or tissue surface. Alternately, the patch can be impregnated with the formulation and applied to the skin or tissue surface to contact active ingredients with the skin while forming the transpiration barrier. A water-impermeable wrap, glove, sock, mitten, or the like can also serve to create a physical barrier. Alternately, or in addition, the transpiration barrier can include a molecular (i.e., chemical) barrier; i.e., one that contains a plurality of molecules or particles that are at least initially unbonded and which dry on or embed in the skin or tissue surface to produce a moisture-resistant barrier. For example, the molecular barrier can include silicone, titanium oxide, polyvinyl alcohol and hydrogels. It should be noted that both a chemical barrier and a physical barrier can be used together or sequentially. In another embodiment, a water-resistant patch is applied to the skin or tissue surface for a period (e.g., 0.5 to 60 minutes) prior to removal of the patch and application of a formula described herein.

In some embodiments, when the formulation comprising an NSAID and a gabapentin family member is applied to the skin, a condition of hypertonicity can be created in the skin or tissue surface local to the area at which the formulation is applied. The hypertonic condition can include an elevated osmotic pressure in the extracellular milieu as compared to the intracellular cytoplasm of the skin cells or of the cells (e.g., endothelial cells) at the tissue surface. This condition of hypertonicity can work cooperatively or synergistically with the other activities provided by the components in the formulation (e.g., the vasoactive activity and/or the chelating activity) to enhance delivery of the active ingredient into and through the epidermis, and/or into and through the basement membrane to the dermis or other tissue underlying the epidermis. In some embodiments, an active ingredient in the formulation that is delivered into and through the epidermis can enter the systemic circulation via the blood system or the lymphatic system.

The high osmolarity of the formulation can continue to exert its effect on cells as the components of the formulation move through the epidermis, compounding or synergizing the effect of the component with vasodilating activity on the movement of the active ingredient within the epidermis and the dermis. In some embodiments, the combination of the active ingredients (e.g., the NSAID and the gabapentin family member), and the pharmaceutically acceptable excipient in the formulation (e.g., a chelator or fasoactive agent) may result in the overall osmolarity of the formulation as a whole being greater than 345 mOsM. This can generate a larger gradient than osmotic pressure generated from the epidermal cell water movement alone and can induce greater physical space between the epithelial cells in which drug molecules can move. This combined and elevated osmotic pressure can continue to drive the active drug ingredient through the basement membrane and into the dermis to deliver the active agent to local dermal or subcutaneous tissues or to the lymph and blood capillaries for systemic distribution.

In accordance with illustrative embodiments of the present invention, a formulation containing gabapentin (or a gabapentin family member) and a nonsteroidal anti-inflammatory drug (NSAID) such as ibuprofen, which can work together in an additive manner or a synergistic manner to reduce pain. Optionally, the formulation includes a penetration enhancer, which can increase the effectiveness of the penetration, also in an additive or synergistic manner.

Although convenient, it is not necessary to include both the NSAID and the gabapentin family member in a single formulation. Rather, the various components can be applied sequentially and in various orders to the skin of a patient so long as the ultimate result is to apply the NSAID (e.g., ibuprofen) and the gabapentin family member at a sufficient concentration of each so that the administered (i.e., applied) NSAID and the administered gabapentin family member are delivered through the skin and into the underlying tissue at concentrations where the NSAID and the gabapentin family member are able to act synergistically to relieve pain at the topical application site.

By "topical application site" is meant the site of skin overlying the point of pain in the tissue or bone, at which site in the skin the topical formulation is applied. Note that the point of pain need not be directly underneath the topical application site but is in the close proximity. For example, a topical application site on the apex of the elbow is at the site overlying pain in the elbow. Thus, in some embodiments, the formulation is topically applied to the site at or near the site of pain in the patient. For example, if the patient has knee pain from, for example, rheumatoid arthritis, the formulation described herein can be topically applied to the skin over the knee cap and/or the skin on the underside of the knee so that it can move through the skin and into the underlying tissue (e.g., at the knee joint). By topical application to an application site at or near the site of the pain, the amount of drug (e.g., ibuprofen) in the formulation administered to the site of the pain is greater than if the formulation were given systemically (e.g., orally or by i.v. injection). By "near" is simply meant not more than one foot, or not more than 9 inches, or not more than 6 inches, or not more than 3 inches, or not more than 1.5 inches away from the site of the pain.

Similarly, a transpiration barrier can also be applied sequentially with respect to the other components one or more times.

In some embodiments, the formulation also includes a chelator (e.g., an ingredient with chelating activity) to sequester the free cations in the interstitial space in the skin, preventing the formation of new intercellular bridges and forcing apart existing bridges, thereby allowing the active ingredients in the formulation to pass through the skin and into the underlying tissue.

Thus, the topical formulations described herein containing at least one active ingredient, such as ibuprofen, gabapentin, or a combination of ibuprofen and gabapentin, promote improved pain management in in vivo animal models of inflammatory and chronic neuropathic pain. The topical formulations were tested by using in vivo animal models of inflammatory and neuropathic pain. Two animal models were used for testing the efficacy and mode of action of cream formulation in pain management. One of the models used was the CFA model (Complete Freud's adjuvant) to induce long term inflammation. Another of the models used was the SNI model (Spared Nerve Injury) for the model of peripheral neuropathic pain. The SNI model is well known (see, e.g., Decosterd and Woolf, Pain 87(2): 149-158, 2000). These studies, and their results, are described below in the Examples section.

The topical formulation containing the NSAID (e.g., ibuprofen) and gabapentin family member (e.g., gabapentin) contains ingredients designed to promote passive penetration (i.e., lipid and osmolyte) through the skin tissue and also in-part to induce a transient vasodilation in the local area that enhances the delivery of the drugs deep into the local tissue. Varadi, G., et al., Randomized Clinical Trial Evaluating Transdermal Ibuprofen for Moderate to Severe Knee Osteoarthritis, Pain Phys., 16: E749-E762, 2013; Carter S G, et al., Methods and Composition for Topical Treatment of Medical Conditions Including Wound and Inflammation, U.S. Pat. No. 8,343,486, Jan. 1, 2013; Carter, S. G., et al., Vasomodulation Influences on the Transdermal Delivery of Ibuprofen, J. Pharm. Sci., 102: 4072-4078, 2013. Application of the formulation enhances drug delivery of the ibuprofen and the second active ingredient (e.g., gabapentin) through eliciting vasodilation and through establishing an osmotic pressure gradient in the tissues, allowing them to transport the drug molecules very effectively, into the dermis, micro-capillaries and lymphatic vessels ("base cream"). The development of this formulation offers an enhanced biological efficacy as the drug concentration will be higher in the local tissue than that with oral delivery, avoids the first pass effect and has shown synergistic effects between gabapentin and ibuprofen, showing that more than one agent can be delivered by the cream. Further, since the efficacious drug dose can be lowered with transdermal delivery, a number of side effects can be minimized or even avoided. Therefore, the combination of a formulation containing a vasodilator and a chelator and/or osmolyte in combination with a drug with known pain-relieving properties (e.g., ibuprofen) represents an outstanding potential for a new product with superior efficacy, due to enhanced delivery of pain-relieving agents to the specific location in the afflicted tissue, reducing the levels of pain experienced by the animal, and eventually by the patient.

Note that for the NSAID ibuprofen, the full name of the ibuprofen drug is 2-[4-(2-methylpropyl)phenyl]propanoic acid, and it has the following structure:

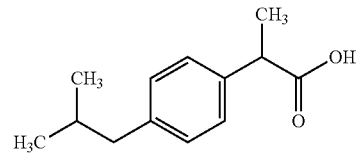

Note that a member of the gabapentin family, the second active ingredient, is gabapentin, a drug that affects the inhibitory neurotransmitter γ-aminobutyric acid (GABA). Gabapentin has the following structure:

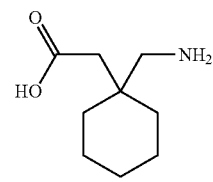 [SMILES: NCC1(CC(=O)O)CCCCC1]

In some embodiments, the amounts of the first ingredient and the second ingredient in the formulation are selected so that the first active ingredient and the second active ingredient work synergistically to treat pain. A formulation containing an NSAID in an amount equivalent to between about 3-10% ibuprofen (e.g., 7.5% ibuprofen) and a gabapentin family member in an amount equivalent to about 5-15%% gabapentin (e.g., 5% gabapentin) work together synergistically. For example, a formulation delivering 7.5% ibuprofen (first ingredient) and 5% gabapentin (second ingredient) are shown below to work synergistically. Amounts of an NSAID such as ibuprofen that work synergistically with a gabapentin family member include, without limitation, an NSAID in an amount equivalent to ibuprofen in a range between about 3% to about 15% ibuprofen including, for example, an amount of NSAID equivalent to ibuprofen in a range of between about between about 3% to about 12%) ibuprofen; an amount of NSAID equivalent to ibuprofen in a range of between about 4% to about 11% ibuprofen; and an amount of NSAID equivalent to ibuprofen in a range of between about 5% to about 10% ibuprofen. Note that all the percentages are in w/w percentage.

Note that an amount of an NSAID equivalent to, for example, 3-10% ibuprofen and an amount of a gabapentin family member equivalent to 5-15% gabapentin are easily determined by a routinely skilled biologist using, for example, the SNI test or the CFA test described in the examples below. Other methods for testing pain are known and can be routinely used. (see, e.g., Piel et al., Gene 537(2): 1840188, 2014)

For example, the Rotarod test can be employed to assess pain. The Rotarod test is a performance test that utilizes a rotating rod onto which a rodent is placed. The rotating rod creates forced motor activity so as to evaluate functional parameters, such as balance and coordination, by measuring riding time (seconds) or endurance. Each animal is trained for 5 minutes at a constant speed of 4 rpm on the rotarod (Rotamex, Columbus Instruments). The first trials start at least 1 hour after training. Every day, each animal receives a number of trials, separated by 30 minutes, at speeds accelerating from 4 to 40 rpm (with a 4 rpm increase every 30 seconds). Each animal is tested for a number of consecutive days (typically 3). Each trial is finished when the animal falls off the rotarod. The latency to falling off the rotarod is recorded and used in subsequent analyses The tail flick test is also a commonly used test to assess pain. Basically, a heat source (e.g., an intense light beam or hot water) is focused on the animal's tail and a timer starts. When the animal flicks its tail, the timer stops and the recorded time (latency) is a measure of the pain threshold.

The hot plate test is another commonly used test to assess pain. Basically, an animal is kept on the heated surface of a plate (e.g., in an enclosed wire mesh or glass). The temperature of the plate is increased and the time of latency between the zero point (when the animal is placed onto the surface or when the heating of the surface starts) and the time when the animal licks its law or jumps to avoid thermal pain.

In some embodiments, an amount of an NSAID such as ibuprofen that works synergistically with 5-15% gabapentin to treat pain with ibuprofen include, without limitation, an NSAID in a range between about 3% to about 10% ibuprofen including, for example, a range of between about between about 4% to about 9% ibuprofen; a range of between about 5% to about 8% ibuprofen; and a range of between about 6% to about 7% ibuprofen. Note that all the percentages are in w/w percentage.

In some embodiments, an amount of a gabapentin family member (e.g., gabapentin) that works synergistically with 3-10% ibuprofen to treat pain include, without limitation, a gabapentin family member in an amount equivalent to gabapentin in a range between about 5% to about 15% gabapentin including, for example, a range of between about between about 6% to about 14% gabapentin; a range of between about 7% to about 13% gabapentin; and a range of between about 8% to about 18% gabapentin. Note that all the percentages are in w/w percentage.

Non limiting amounts of combinations contemplated in the formulations described herein include: 3% to 10% ibuprofen plus 5-15% gabapentin (e.g., 7.5% ibuprofen plus 5% gabapentin or 8% ibuprofen plus 6% gabapentin). Note that all the percentages are in w/w percentage.

Other amounts of the first and second ingredient are contemplated.

In some embodiments, the amount of the first ingredient is greater than or equal to the amount of the second ingredient in the formulation. For example, the formulation may contain 7% ibuprofen and 6% gabapentin. In some embodiments, the amount of the first ingredient is 1.5 times greater than the amount of the second ingredient in the formulation. For example, the formulation may contain 7.5% ibuprofen and 5% gabapentin.

In some embodiments, the amount of the first ingredient is less than or equal to the amount of the second ingredient in the formulation. For example, the formulation may contain 5% ibuprofen and 6% gabapentin. In some embodiments, the amount of the first ingredient is 1.5 times less than the amount of the second ingredient in the formulation. For example, the formulation may contain 5% ibuprofen and 7.5% gabapentin.

In another embodiment, a kit for topical delivery of an active ingredient to a patient is provided. The kit's components include an NSAID such as ibuprofen as a first active ingredient in an amount equivalent to about 3-10% ibuprofen; and a gabapentin family member as a second ingredient in an amount equivalent to about 5-15% gabapentin. Optionally, the kit includes one or more additional components (e.g., a transpiration barrier such as a plastic bandage). Optionally, the kit also includes a set of written instructions for use, by or on said patient, of the components of the kit according to one of the methods of topical delivery described herein.

In another embodiment, the invention provides a method of manufacturing a medicament for topical delivery of an active ingredient. The method includes combining components an NSAID such as ibuprofen in an amount equivalent to about 3-10% ibuprofen, and a gabapentin family member such as gabapentin in an amount equivalent to about 5-15% gabapentin.

Vertebrate animals were used for neuropharmacological studies. Rodents, such as the ones used in these experiments, have been used extensively for decades to study the sensory nervous system. Rats have proven to have distinct and specific value to neuranatomical, pharmacological studies and studies of analgesic efficacy; therefore, this species has been selected for evaluation in this study. Rats were used to determine the efficacy of the transdermal cream. Rats were amenable for their size and easy access to the central nervous system. The direct and reliable access to the spinal cord was achieved through the intrathecal injection technique described in Hylden and Wilcox, Eur. J. Pharmacol. 67(2-3): 313-316, 980; Mestre et al., J. Pharmacol. Toxicol. Methods 32(4): 197-200, 1994. Two models were used—Complete Freund's Adjuvant (CFA)-induced thermal hyperalgesia and spared nerve injury (SNI) mechanical hyperalgesia models.

Baselines were established for all rats for thermal response latency before intraplantar (i.pl.) injection of the inflammatory agent. Three days after injection of the inflammatory agent (CFA), the degree of thermal hypersensitivity was determined followed by topical application to anesthetized rats of i) the drug-free cream, creams containing ii) ibuprofen, iii) gabapentin, and each the combination of ibuprofen with gabapentin using a topical cream optimized for deep skin penetration/vascular access. Six experimental groups were used in total Application of ibuprofen cream served both as an active pharmacological agent and positive control throughout these studies. The drug formulation and control cream (negative control) was applied to the glabrous side of the rat hindpaw using a previously published method. Nozaki-Taguchi, N. and T. L. Yaksh., Characterization of the Antihyperalgesic Action of a Novel Peripheral Mu-opioid Receptor Agonist-loperamide, *Anesthesiology*, 90: 225-234, 1999; Iadarola, M. J., et al., Increased Spinal Cord Dynorphin mRNA During Peripheral Inflammation, *NIDA Re.s Monogr.*, 75: 406-409, 1986.

Rats were isoflurane-anesthetized (1-2%) and the cream (0.2 g) applied gently with a finger for 1 minute to the glabrous skin of the hindpaw. For low drug concentrations, 5% formulations of all drugs were. For high drug concentrations, 10% cream formulations were employed. Excess formulation remains on the skin surface for 30 minutes and was then removed under anesthesia. Upon recovery from anesthesia (within 10 minutes of cessation of anesthetic), rats were moved to plexiglass enclosures for sensory assessment. Efficacy was initially tested at 1, 2, 4, 8, 24 hours after cream treatment; depending on initial results. Time was revised to track the onset and offset of drug effects.

Example 1: Synergistic Action of Ibuprofen and Gabapentin in an Inflammation Model. CFA Testing Two parallel studies (two arms) were done, each with four treatment groups, with four Sprague-Dawley rats per group. The rats used were male rats weighing 175-200 grams. Half of the rats were given injections of 1:1 complete Freund's adjuvant (CFA) on day 0 to produce long-term inflammation of the left hindpaw; the other half of the rats were given spared nerve injury (SNI, transection of 2 of 3 branches of the sciatic nerve) in the lower thigh on day 0.

Before treatments, rats' baseline response thermal latencies (on a glass surface suspended above a moveable heat lamp) or mechanical thresholds (on a wire mesh surface suspended above a moveable electronic von Frey stimulator) were determined after 15 min acclimatization on the thermal or mechanical testing apparatuses.

The CFA model of persistent inflammatory hyperalgesia in one hindpaw of the rats was utilized (see Gold and Gebhart, Nature Medicine 16: 1248-1257, 2010). This model produces edema, reddening, inflammation, and behavioral hypersensitivity. Experimental groups of rats were anesthetized with isoflurane before receiving an intraplantar injection into the left hindpaw of 100 µl of CFA (1:1 with sterile PBS) using a sterile 0.5 ml syringe. The CFA model produced inflammatory signs accompanied by thermal and mechanical hyperalgesia in the injected hindpaw within six to eight hours. The hypersensitivity peaks at 3 days, which was the first testing day of the analgesic topical formulations in the CFA model.

One of four treatments was applied to each rat on days 3, 7 and 11 after CFA injection or on days 7, 14 and 21 after SNI application. The four treatments were: (i) control cream which did not contain any active drug, (ii) formulation with ibuprofen 10%, (iii) formulation with ibuprofen 7.5%+ gabapentin 5%, and (iv) formulation with gabapentin 5%. For the formulations with ibuprofen and/or gabapentin, the formulation also contained vasodilators arginine and methyl nicotinate, chelator EDTA, solvents dimethyl acetamide and water, osmolyte potassium hydroxide, lipids soy bean oil and olive oil, and various other excipients including eucalyptol, gelcarin GP-379NF, glyceryl monostearate, menthol, methyl paraben, propylparaben, phenoxyethanol, permulen TR-1, phospolipon 90H, ST elastomer, urea, and Vitamin E TPGS.

For application of the topical formulation, the rats were anesthetized with isoflurane for 30 min. while the creams were applied to both hindpaws to minimize oral absorption as described in Nozaki-Taguchi et al., Anesthesiology 90: 225-234, 1999; Iadarola et al., NIDA Res. Monogr. 75: 406-409, 1986. Briefly, 0.2 grams of the topical formulation was applied gently with a finger for one minute to the glaborous skin of the hindpaw of each anesthetized rat. For a formulation with 10% ibuprofen, 0.2 grams of formulation meant that 20 mg ibuprofen was administered. For a formulation with 5% gabapentin, 0.2 grams of formulation meant that 10 mg gabapentin was administered. For a formulation with 7.5% ibuprofen and 5% gabapentin, 0.2 grams of formulation meant that 15 mg ibuprofen and 10 mg gabapentin was administered.

The efficiency of transdermal delivery (approximately 10%) drastically reduces the actual drug doses administered to the rat. Excess formulation remains on the skin surface for 30 minutes and was then removed under anesthesia. Upon recovery from anesthesia (within 10 minutes of cessation of anesthetic), rats were moved to plexiglass enclosures for sensory assessment.

Upon awakening, for the thermal sensory response testing, the rats were transferred to the thermal testing apparatus. This apparatus was a glass platform in plastic enclosures (with air holes on four sides and the top). After 15 minute on the enclosed glass platform for acclimatization, their thermal response latencies were determined at 3 post-treatment time points: 1 hour, 4 hour and 24 hour. The behavioral endpoint was the paw withdrawal latency to application of a radiant light source delivering 49°–55° C. of radiant heat to the plantar surface of the paw. The stimulus was terminated completely after 15 seconds or immediately following paw withdrawal. For each paw, the withdrawal latency was determined by averaging three measurements separated by at least 1 min.

In these studies, the sensory responsiveness to thermal (radiant heat) stimuli was assessed in terms of time to elicit paw withdrawal. Measurements were taken prior to CFA injection and following several days after inflammation (FIGS. 1A-1C) or nerve injury (FIGS. 3A-3C). Sensory responses to mechanical stimulus (von Frey stimulation) were also assessed prior to CFA injection and following several days after inflammation (FIGS. 2A-2C) or nerve injury (FIGS. 4A-5C). In FIGS. 1A-5C the term baseline or "BL" refers to the first measurement on the test day prior to administration of drug. Once the magnitude of hypersensitivity was established, the subjects were anesthetized with isoflurane and the treatments formulated in cream were applied to the plantar skin of the hindpaws. After 20 minutes, the subjects were allowed to regain consciousness, were placed on the testing apparatus, and measurements taken at various hours post-treatment.

In the data shown in FIGS. 1A-5C, the ipsilateral hindpaw treatment groups were compared by one-way ANOVA with a Dunnett's posthoc test for multiple comparisons to a control (vehicle treatment group). *indicates significance at p<0.05 with Dunnett's post-hoc test for multiple comparisons to a control. Note that in the CFA-set B experiment, some of the groups failed to manifest hyperalgesia; the reason for this deviation is unknown. However, this outcome provided an inadvertent negative control: none of the treatments elicited an analgesic effect, validating the antihyperalgesic nature of the treatment effects in the other experiments.

The results of the CFA testings (yielding CFA inflammation-induced hyperalgia) are shown as follows: FIGS. 1A, 1B, and 1C are CFA set A, thermal response at days 3, 7, and 12, respectively; FIGS. 2A, 2B, and 2C are CFA set A, mechanical response at days 3, 7, and 12, respectively. Note that FIGS. 1A-5C, the square symbols are data from the application to the hindpaw of a formulation containing a vasodilator plus 10% ibuprofen, the triangles are data from the application to the hindpaw of a formulation containing 7.5% ibuprofen plus 5% gabapentin, the diamonds are data from the application to the hindpaw of a formulation containing 5% gabapentin, and the circles are data from the application to the hindpaw of a formulation no ibuprofen or gabapentin. Note that in FIGS. 1A-5C, the color or filled in symbols are the inflamed hindpaws (inflamed from CFA application) (FIGS. 1A-2C) and the spared nerve injury hindpaws (FIGS. 3A-5C) and the gray-filled symbols being the control hindpaws in the inflamed hindpaws (inflamed from CFA application) (FIGS. 1A-2C) and the spared nerve injury hindpaws (FIGS. 3A-5C). Note, however, that in FIGS. 1A-5C, the control formulation in the inflamed (inflamed from CFA application) (FIGS. 1A-2C) and the spared nerve injury hindpaws (FIGS. 3A-5C) is filled in with the color white whereas the control formulation in the control hindpaws in FIGS. 1A-5C are filled in with the color gray.

Three days after injection of the inflammatory agent (CFA), the degree of thermal hypersensitivity was determined followed by topical application to anesthetized rats of i) the drug-free cream, creams containing ii) ibuprofen, iii) gabapentin, and each the combination of ibuprofen with gabapentin. Ibuprofen, gabapentin and their combination may have produced thermal antihyperalgesia on day 3 at 2 and 4 hours after treatment, but these changes were borderline significant; this possible efficacy was not repeated on days 7 and 12 post-CFA (FIG. 1A-1C). For mechanical hyperalgesia, the combination was efficacious on days 7 and 11 at 2 hours after treatment, and both agents were efficacious when given alone on day 12 again at 2 hours after treatment (FIG. 2A-2C).

As the results show, the vehicle treatment did not alter thermal and mechanical sensitivity in either animal model. As shown in FIGS. 1A-1C, the ipsilateral (CFA-treated) foot became more sensitive to the thermal stimulus. Application of the cream containing ibuprofen only (colored filled square line in FIGS. 2A-2C) for 20 minutes completely reversed the hyperalgesia at 1 hour after treatment on day 3 post-CFA. The beneficial impact of the drug lasted for 4 hours and the hyperalgesia completely returned to the baseline level after 24 hours; the ibuprofen effect was statistically significant. Transdermal delivery of gabapentin only failed to suppress thermal hyperalgesia in the same model (see colored filled diamond line in FIGS. 1A-1C), but the combination trended to increasing efficacy in suppressing mechanical hyperalgesia on days 7, 11 (data not shown) and 12 post-CFA.

Example 2: Synergistic Action of Ibuprofen and Gabapentin in a Peripheral Nerve Injury Model The spared nerve injury (SNI) model was used for a model of peripheral nerve injury. Peripheral nerve injury in patients often results in the development of hypersensitivity to stimuli that are normally not noxious. The lateral surface of the left thigh of each rat was shaved and an approximately 1.5 cm long incision was made along a line connecting the posterior end of the iliac crest and the knee joint. The muscles were separated to expose the sciatic nerve and its three terminal branches (tibial, common peroneal, and sural). The common peroneal and tibial nerves were ligated with a 5.0 silk suture and sectioned distal to the ligation, removing 2-4 mm of the distal nerve stump. The muscle were then replaced over the nerve and the skin incision closed with surgical staples. In the sham surgery (the control), the nerve will be exposed but not manipulated. Testing of the topical formulations began on day 3 post surgery.

Upon awakening, for the mechanical sensory response testing, the rats were placed on a wire mesh platform in a glass enclosure and allowed to acclimate to their surroundings for a minimum of 15 minutes before testing. The threshold of the subject's paw withdrawal responses to application of an electronic von Frey stimulator tip to the plantar surface of the hindpaw was recorded. A stimulus of sufficient force elicited a paw lick or withdrawal. von Frey thresholds (for mechanical testing) were determined at 4 post-treatment time points: 1 hour, 2 hour, 4 hour and 24 hour. The SNI results (yielding nerve injury-induced hyperalgesia) are shown as follows results are shown as follows: FIGS. 3A, 3B, and 3C are SNI set A, thermal response at days 6, 7, and 21, respectively; FIGS. 4A, 4B, and 4C are SNI set A, mechanical response at days 6, 7, and 21, respectively; FIGS. 5A, 5B, and 5C are SNI set B, mechanical response at days 7, 14, and 21, respectively.

In the spared nerve injury model (SNI) there was no efficacy in thermal hyperalgesia for all drug and drug combination treatments on any day at any time (FIG. 3A-3C), but the combination of ibuprofen and gabapentin had some efficacy against mechanical hyperalgesia at 2 hours on day 7 and 1 hour on day 11 (FIG. 4A-4C,). This efficacy repeated in the replicate SNI experiment (FIG. 5A-5C) (but only at 2 hours), increasing confidence in this finding. In the SNI model, the combination of the two drugs produced progressively increasing efficacy against mechanical hyperalgesia on days 7, 14 and 21, and these effects were statistically significant (see colored filled diamond line in FIGS. 4A-4C and 5A-5C).

Thus, as the data shows (see, e.g., FIGS. 1A-1C), ibuprofen and the combination treatment demonstrated significant reversal of thermal hypersensitivity at some time points during the testing period. The data also show (see FIG. 5C, for example), the combination treatment of ibuprofen and gabapentin (7.5% and 5%, respectively) demonstrated significant reversal of mechanical hypersensitivity at some time points during the testing period. This reversal was more than merely additive for ibuprofen alone or gabapentin alone; rather, it is clear that the gabapentin and ibuprofen are acting synergistically to reverse mechanical hypersensitivity.

In two of the groups, hyperalgesia was evident and the treatment elicited an effect consistent with the CFA-set A experimental cohort (FIGS. 1A-2C). Therefore, a replicate of the positive findings with the combination of ibuprofen+ gabapentin was observed.

For the CFA (complete Freund's adjuvant) injected animals, ibuprofen and the combination of ibuprofen plus gabapentin may have produced thermal antihyperalgesia on day 3 at 2 and 4 hours after treatment, but these changes were borderline significant; this possible efficacy was not repeated on days 7 and 11 post-CFA. For mechanical hyperalgesia, the combination was efficacious on days 7 and 11 at 2 hours after treatment, and both agents were efficacious when given alone on day 11 again at 2 hours after treatment.

For the spared nerve injury (SNI) applied animals, there was no efficacy in thermal hyperalgesia on any day at any time, but the combination had some efficacy against mechanical hyperalgesia at 2 hours on day 7 and 1 hour on day 11. This efficacy repeated in the replicate SNI experiment (but only at 2 hours), increasing confidence in this finding.

Overall, the results shown in FIGS. 1A-5C offer a proof of concept for the utility of using the topical creams described herein for the delivery of analgesics and antihyperalgesic agents to subjects.

In summary, these results of Examples 1 and 2 have demonstrated that several drugs can be effectively delivered transdermally in human and animal models in the skin and in the neighboring tissues. In addition, these studies provide evidence that transdermally delivered ibuprofen (anti-inflammatory) and gabapentin (antiepileptic & antinociceptive) can be applied topically to suppress pain due to inflammation and peripheral nerve injury. Without wishing to be bound by a particular theory, the gabapentin and ibuprofen may act through inhibiting immune and inflammatory responses and through inhibition of sensory neuron hyperexcitability.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A topical formulation for treatment of pain in a patient, comprising:
   a. a first active ingredient, wherein the first active ingredient is a nonsteroidal anti-inflammatory agent in an amount equivalent to 3-15% ibuprofen,
   b. a second active ingredient, wherein the second active ingredient is a gabapentin family member in an amount equivalent to about 5-15% gabapentin,
   c. an osmolyte, and
   d. a lipid component;
   wherein the osmolarity of the formulation is greater than 345 mOsM.

2. The formulation of claim 1, wherein the first active ingredient is ibuprofen.

3. The formulation of claim 1, wherein the first active ingredient is selected from the group consisting of aspirin, elecoxib, diclofenac, diflunisal, etodolac, ibuprofen, indomethacin, ketoprofen, ketorolac, nabumetone, naproxen, oxaprozin, piroxicam, salsalate, sulindac, tolmetin.

4. The formulation of claim 1, wherein the second active ingredient is gabapentin.

5. The formulation of claim 1, wherein the second active ingredient is pregabalin or atagabalin.

6. The formulation of claim 1, wherein the formulation further comprises a vasoactive agent.

7. The formulation of claim 1, wherein the formulation further comprises a chelator.

8. The formulation of claim 1, wherein the formulation further comprises a penetration enhancer.

9. The formulation of claim 1, wherein the formulation is applied at or near a site of the pain.

10. The formulation of claim 1, wherein topical application of the formulation to the patient does not permanently damage cells of the patient.

11. The formulation of claim 1, wherein the patient is human.

12. A method for treating pain in a patient comprising administering the formulation of claim 1 at or near a site of pain in the patient.

* * * * *